United States Patent
Barakat et al.

(10) Patent No.: US 7,055,526 B2
(45) Date of Patent: Jun. 6, 2006

(54) ANTI-SNORING DEVICE COMPRISING A SKIN COMPATIBLE ADHESIVE

(75) Inventors: Mohammed A. Barakat, Pescara (IT); Gianfranco Palumbo, Eschborn (DE)

(73) Assignee: Mohamed Ali Bakarat, Brussels (BE)

( * ) Notice: Subject to any disclaimer, the term of this patent is extended or adjusted under 35 U.S.C. 154(b) by 35 days.

(21) Appl. No.: 10/360,676

(22) Filed: Feb. 7, 2003

(65) Prior Publication Data

US 2003/0149387 A1    Aug. 7, 2003

Related U.S. Application Data

(63) Continuation of application No. PCT/US01/24865, filed on Aug. 8, 2001.

(30) Foreign Application Priority Data

Aug. 9, 2000    (EP) ................................ 00117093

(51) Int. Cl.
A61F 5/56    (2006.01)
(52) U.S. Cl. ............ 128/848; 128/206.12; 128/206.14; 128/206.19; 128/206.24; 128/206.25
(58) Field of Classification Search .......... 128/201.17, 128/206.12, 206.14, 206.19, 200.24, 848, 128/206.21, 206.24, 206.25
See application file for complete search history.

(56) References Cited

U.S. PATENT DOCUMENTS

| | | | | |
|---|---|---|---|---|
| 1,354,652 A | * | 10/1920 | Jefferies | 128/857 |
| 2,310,082 A | * | 2/1943 | Holbrooke | 602/55 |
| 2,399,545 A | * | 4/1946 | Davis | 604/389 |
| 2,574,623 A | * | 11/1951 | Clyde | 128/848 |
| 2,928,388 A | * | 3/1960 | Jaroslaw | 128/206.14 |
| 3,049,121 A | * | 8/1962 | Brumfield et al. | 128/260.14 |
| 3,342,183 A | * | 9/1967 | Edenbaum | 604/307 |
| 3,695,265 A | * | 10/1972 | Brevik | 128/206.14 |
| 4,354,489 A | * | 10/1982 | Riaboy | 128/206.14 |
| 4,467,799 A | * | 8/1984 | Steinberg | 128/206.14 |
| 4,817,636 A | * | 4/1989 | Woods | 128/848 |
| 5,561,863 A | * | 10/1996 | Carlson, II | 2/206 |
| 5,714,225 A | * | 2/1998 | Hansen et al. | 428/114 |
| 5,735,270 A | * | 4/1998 | Bayer | 128/206.14 |
| 5,842,470 A | * | 12/1998 | Ruben | 128/206.19 |
| 6,029,667 A | * | 2/2000 | Lurie | 128/207.16 |
| 6,089,232 A | * | 7/2000 | Portnoy et al. | 128/848 |
| 6,116,236 A | * | 9/2000 | Wyss | 128/200.24 |
| 6,308,330 B1 | * | 10/2001 | Hollander et al. | 2/9 |
| 6,341,606 B1 | * | 1/2002 | Bordewick et al. | 128/206.25 |
| 6,460,539 B1 | * | 10/2002 | Japuntich et al. | 128/205.27 |
| 6,484,722 B1 | * | 11/2002 | Bostock et al. | 128/206.19 |
| 6,520,181 B1 | * | 2/2003 | Baumann et al. | 128/206.19 |
| 6,543,450 B1 | * | 4/2003 | Flynn | 128/206.19 |
| 6,544,642 B1 | * | 4/2003 | Cinelli et al. | 428/343 |

FOREIGN PATENT DOCUMENTS

EP    0 353 972 A1 *    7/1990

* cited by examiner

Primary Examiner—Glenn K. Dawson
Assistant Examiner—Michael Mendoza
(74) Attorney, Agent, or Firm—Young & Thompson

(57) ABSTRACT

Anti-snoring devices, more specifically to externally worn anti-snoring devices covering essentially a wearer's mouth and being adhesively attached to a wearers skin in the peri-oral area are described. The articles utilise an improved adhesive so as to facilitate easy application and removal of the article from the wearer, whilst ensuring maintenance of the article in the desired position. In particular the adhesives provide attachment on greasy and oily skin.

16 Claims, 1 Drawing Sheet

ANTI-SNORING DEVICE COMPRISING A SKIN COMPATIBLE ADHESIVE

CROSS REFERENCE TO PRIOR APPLICATION

This is a continuation of International Application PCT/US01/24865, with an international filing date of Aug. 8, 2001, and published in English.

FIELD OF THE INVENTION

The present invention relates to an anti-snoring devices, more specifically to externally worn anti-snoring devices covering essentially a wearer's mouth and being adhesively attached to a wearers skin in the peri-oral area. The articles utilise an improved adhesive so as to facilitate easy application and removal of the article from the wearer, whilst ensuring maintenance of the article in the desired position. In particular the adhesives provide attachment on greasy and oily skin.

BACKGROUND OF THE INVENTION

Some different approaches have been taken in the filed of anti-snoring devices, and a number of patents disclose devices intended to be worn externally in the facial area.

U.S. Pat. No. 1,354,652, issued on Oct. 5, 1920, discloses a strip of adhesive material which can be worn over the mouth and which is intended to prevent mouth breathing and further to harmonise the facial features of a wearer, by more evenly balancing the muscles of expression. The face of the entire strip is covered with a suitable adhesive substance.

U.S. Pat. No. 4,817,636, issued on Aug. 4, 1989, discloses an anti-snoring device comprising a sheet of flexible material comprising a hypoallergenic adhesive on its back. The adhesive is further described as preferably sterile, pressure-sensitive adhesive to be applied as a film on the back face of the sheet of material. The device is designed to prevent intake of air through the mouth.

U.S. Pat. No. 5,640,974, issued on Jun. 24, 1997, and U.S. Pat. No. 5,690,121, issued on Nov. 25, 1997, disclose kits to promote effective breathing through the nasal passage. These kits are said to reduce the loudness of snoring or to eliminate snoring all together. The kits comprise a chin support member fitting underneath the user's mouth, but not covering the central portion of the mouth or even the full lips of the user.

JP 11076286, published on Mar. 23, 1999, discloses an adhesive tape for stertor prevention which comprises a net-like portion.

DE 3837277, published on May 10, 1990, discloses an anti-snoring device designed to prevent opening of the mouth during the sleep. The device comprises an adhesive tape which has an orifice, perforation or notch in a central area where it thereby can tear apart easily.

Devices covering the respiratory organs can also be found in the field of protective masks. These devices are typically provided with headbands and cover mouth and nose of a wearer. Such devices are disclosed for example in U.S. Pat. No. 5,724,964, issued on Mar. 10, 1998, and in U.S. Pat. No. 5,735,270, issued on Apr. 7, 1998. U.S. Pat. No. 4,240,420, issued on Dec. 23, 1980, and its continuation-in-part U.S. Pat. No. 4,354,489, issued on Oct. 19, 1982, disclose filter masks which comprise separate filter elements for the nose and for the mouth of a wearer.

The prior art in the general field of adhesives for attachment to the skin is particularly developed in the field of articles such as band-aids, plasters and bandages. These articles are however typically applied in an emergency situation, where for example, a cut into the skin of the wearer has occurred and absorption of the body liquids emanating from a wound is desired. In this context performance aspects of the article such as easy application and use of the product, comfortable wear as well as painless removal, and discreteness are again subordinate, to other criteria in this case such as sterility, healing support, and mechanical protection of the wound. Also such wound covering absorbent articles are mostly adhered to the skin where prior to application of the absorbent article bodily hair can be removed or where little hair grows.

In order to provide the desired level of adhesion of such bandages, the prior art typically discloses the utilisation of certain adhesives having very high cohesive strengths such as rubber based adhesives and acrylics. These adhesives are then applied as thick layers to maximise the adhesive force by which the bandage is secured to the skin of the wearer.

U.S. Pat. No. 4,699,146 discloses hydrophilic elastomeric pressure sensitive adhesives suitable for use with ostomy devices, bandages, ulcer pads, sanitary napkins, diapers, and athletic padding. The adhesive comprises at least one uradiation cross linked organic polymer and an adhesive plasticizer.

GB 2 115 431 discloses adhesives for bandages, wounds or burn dressings, EKG adhesives, sanitary napkins, diapers and ulcer pads. The adhesive comprises an irradiation cross linked organic polymer such as polyvinylpyrrolodine and an adhesive plasticizer.

However, for satisfactory use with an anti-snoring device, which may be worn each night, it is important that the adhesive has a skin compatible composition and not be harsh or aggressive towards the skin or cause skin irritation or inflammation. Also it is preferred if the adhesive is compliant with the skin of the wearer such that maximum skin surface contact between the adhesive and the skin is achieved. Moreover, it is also desirable to provide an adhesive such that the anti-snoring device can be readily removed from the wearer, without the wearer experiencing any unacceptable pain level. This is particularly important under circumstances, where the device is removed and reapplication of the device once or even a number of times is required for example to allow for better communication or intake of medicine, and to ensure the application of such devices on sensitive skin, e.g. of an elderly wearer. However, on the other hand the desired level of adhesion, albeit painless should of course also be maintained during such multiple applications of the device.

The problem of achieving the desired adhesion level is further exacerbated under wet skin conditions. In some cases, prior to the placement of the device the skin is cleaned and is usually as a result moist. The currently available adhesives, such as those containing hydrocolloid particles, however often do not immediately strongly adhere to the skin and may need to be held in place until sufficient minimum adhesion occurs. Moreover, the overall adhesive ability of such adhesives tends to be significantly reduced on wet skin surfaces per se, so that the device will typically not remain attached to the skin during wear if any pressure is exerted onto the device, for example by facial movements.

Moist and wet skin however is not just a problem which is prevalent at the device application stage as a significant amount of moisture is also generated during the use of the device from the wearer by perspiration and from moisture contained in the exhaled air. Under such circumstances currently available adhesives typically cannot absorb this moisture and again the adhesive strength is reduced to such an extent that the device will often become detached during wear. It is hence very important to provide an adhesive which provides both initial adhesion and maintenance of its adhesive strength on wet skin.

Another problem which is particularly prevalent for anti-snoring device usage is the ability of the adhesive to adhere on greasy or oily skin surfaces. The levels and types of grease and sebum naturally present on the skin vary from person to person. In addition, the wearers of such devices may want to utilise creams such as moisturising creams or other pharmaceutical creams on the area of skin typically in contact with the adhesive of the device. Thus it is also highly desirable that the adhesive exhibits an ability to adhere to greasy skin.

None of the prior art in the field of skin compatible adhesives however even recognises or addresses the problem of providing these devices with an adhesive which meets these criteria, in particular adhesives which adhere to wet skin or adhesives which adhere to oily and greasy skin and maintain their adhesiveness thereon.

For example, WO-A-97/24149 (3M) describes a lipophilic polar pressure sensitive adhesive stated to have enhanced adhesion to greasy skin, the adhesive including a hydrophilic polymer matrix, a polar organic plasticiser and at least 9 wt % of a surfactant having an HLB (hydrophile lipophile balance) value of 10 to 17. It is stated generally that the hydrophilic polymer matrix may be selected from a range of polymers including homo- and copolymers of, for example, (meth)acrylic acid and salts thereof, acrylamide, N-vinyl pyrrolidone and acrylamidopropane sulphonic acid and salts thereof. The adhesive is prepared by polymerisation in a homogeneous aqueous mixture.

The adhesive disclosed in WO-A-97/24149 is stated to have utility in biomedical electrodes, mammalian skin coverings and pharmaceutical delivery devices. However, only acrylic acid homopolymer and N-vinyl pyrrolidone homopolymer based adhesives are specifically exemplified in the working Examples. The presence of a hydrophobic monomer and/or polymer is not described.

U.S. Pat. No. 5,338,490 (Dietz et al), describes a two-phase composite pressure sensitive adhesive having discontinuous hydrophobic pressure sensitive adhesive domains within a continuous hydrophilic phase. The adhesive is stated to be ionically conductive regardless of the amount of water present, whereby the adhesive is stated to have utility in biomedical electrodes.

In view of the prior art mentioned above there still exists a need to provide an improved anti-snoring device which meets the following objectives:

The device efficiently promotes nasal breathing and thereby reduces or prevents snoring.

The device is comfortable and safe to wear.

The device is cheap to manufacture, so that it can serve as a disposable article, however, may alternatively be reusable many times.

The device allows for facial movement, namely to at least somewhat open the mouth, to speak, to cough and the like.

The device can be provided in one size to fit a large variety of consumers.

The devices can be attached to wet and/or greasy skin.

The device reliably adheres to human skin over extended periods of time.

It is another objective of the present invention to provide an adhesive, in particular of an anti-snoring device, that exhibits an ability to adhere to skin upon reapplication, particularly multiple reapplication whilst still allowing painless removal.

It is another object of the present invention to provide an adhesive, in particular of an anti-snoring device, which upon removal from the skin of the wearer leaves no residues.

It is yet another object of the present invention to provide an adhesive, in particular of an anti-snoring device, which does not cause a cold or otherwise unacceptable temperature sensation upon application to the wearer.

An additional object of the present invention to provide an adhesive, in particular of an anti-snoring device, which provides flexibility, stretchability and contractability so that it is able to adapt to the contours of the face during all bodily movements and hence be comfortable for the wearer of the device, whilst still having sufficient adhesive capacity to ensure secure attachment during use.

It has now been surprisingly found that the above objectives can be meet by providing the anti-snoring device with the mechanical properties as defined hereinafter and comprising an adhesive as defined hereinafter.

SUMMARY OF THE INVENTION

The present invention relates to a anti-snoring devices, more specifically to externally worn anti-snoring devices covering essentially a wearer's mouth and being adhesively attached to a wearers skin in the peri-oral area. The articles utilise an improved adhesive so as to facilitate easy application and removal of the article from the wearer, whilst ensuring maintenance of the article in the desired position. In particular the adhesives provide attachment on greasy and oily skin.

Claimed and described is an anti-snoring device (10) for placement over the mouth of wearer, comprising a flexible sheet of material having a central mouth portion (16) and a peripheral portion (18) and a wearer facing side (12) and an ambient facing side (14), wherein at least a portion of said mouth portion (16) is adhesive free and wherein said peripheral portion (18) is provided with a discontinuous application of adhesive on the wearer facing side (12).

Further claimed and described is an anti-snoring device (10) for placement over the mouth of wearer, the device comprising a flexible sheet of material, the sheet having a wearer facing side and a garment facing side, comprising on the wearer facing side an adhesive, wherein said adhesive has dry peel strength ($P_{DI}$) and a greasy peel strength ($P_{GI}$) as defined in the test method herein wherein the ratio of $P_{DI}$ to $P_{GI}$ is from 1:1 to 1.0:0.2.

BRIEF DESCRIPTION OF THE DRAWINGS

It is believed that the invention will be better understood in conjunction with the accompanying drawings in which.

DETAILED DESCRIPTION OF THE INVENTION

Figure 1:
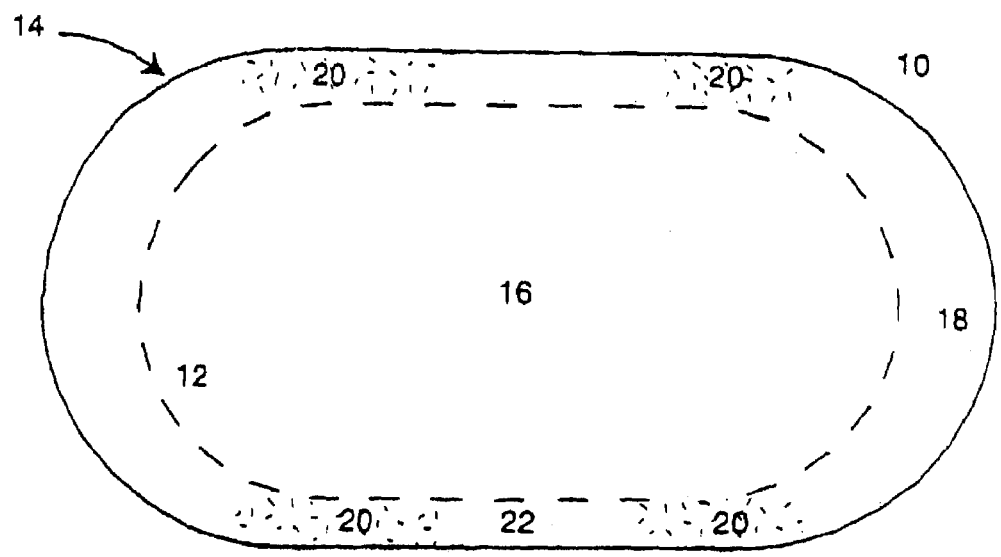
FIG. 1 is a top view onto the wearer facing side of a preferred embodiment of the present invention.
Figure 2:
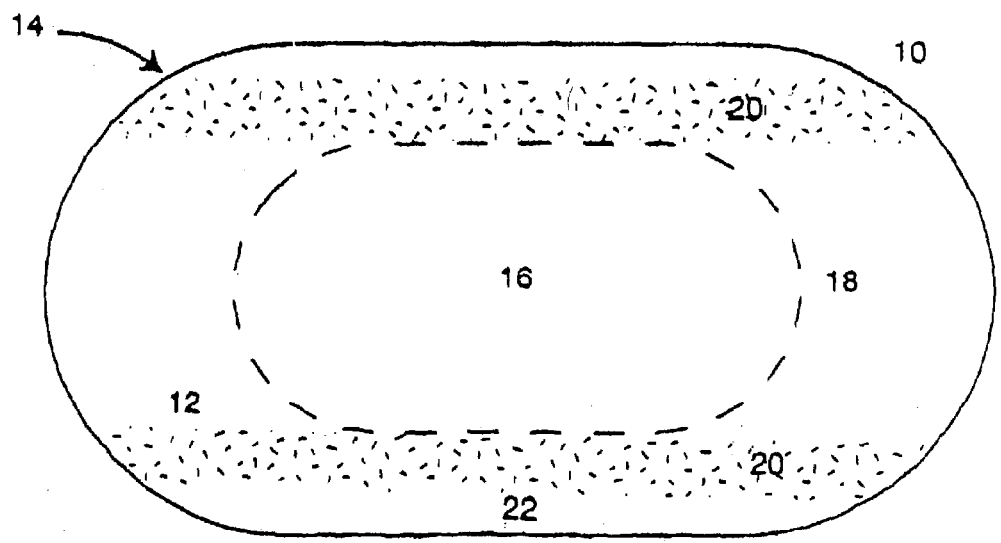
FIG. 2 is a top view onto the wearer facing side of another preferred embodiment of the present invention.

An anti-snoring device (10) provided in accordance with the present invention comprises as a key element a flexible sheet of material. As shown in FIG. 1 and FIG. 2, the sheet comprises a wearer facing side (12), an ambient facing side (14), a mouth portion (16) and a peripheral portion (18). The mouth portion (16) is generally in the centre of the sheet.

The flexible sheet can be provided from a variety of materials and a variety of combinations of materials. Preferred materials include non-woven materials, textile materials, e.g. silk, linen or cotton, and tissue paper. Also may any material be employed with in known in the art of absorbent articles, namely sanitary napkins, panty liners and diapers, for use as a topsheet or as a backsheet of such absorbent articles. Materials known for use in a topsheet provide good liquid permeability and hence also good air permeability, while they are appropriate for skin contact. Materials known for use in a backsheet provide typically a lesser degree of air permeability, but recently developed materials provide such a high vapour and air permeability, that they may well be considered for the present use. Due to the humidity of the exhaled air, materials which provide good vapour permeability are highly preferred, as to avoid an moist feeling during wear of the anti-snoring device.

While the present invention is not limited to air-permeable flexible sheets, air-permeable flexible sheets are preferred. This can be understood from the following considerations:

Without wishing to be bound by theory, it is believed that snoring can be attributed to breathing through the open mouth. This causes the tongue to move to the back of the throat restricting airflow and causing vibration of the soft palate (the snore). Keeping the mouth closed will promote nasal breathing and keeping the tongue forward and thereby lead to a smooth airflow and in most cases reduce or suppress snoring.

According to the present invention it has been found that a breathable sheet of material to control the air flow suffices to largely reduce or fully suppress snoring, hence giving the wearer the freedom to still somewhat open the mouth. It is believed, that the selection of the appropriate, breathability of the flexible sheet allows to provide an efficient anti-snoring device (10), even if the mouth of a wearer is wide open. Also will the anti-snoring device (10), even if the mouth of a wearer is open, prevent the drying out of the mouth which is beneficial for the soft palate and uvula, which otherwise tend to harden over years of mouth breathing.

The anti-snoring device (10) of the present invention may have any shape, such as circular, oval, squared, rectangular or triangular. Oval shapes are preferred. If provided for a adult wearer the sheet should be shaped have a width from 5 cm to 12 cm, preferably 7 cm to 9 cm, measured in the horizontal direction (from the left to the right corner of the mouth) and a height from 2 cm to 10 cm, preferably 3 cm to 8 cm, more preferably 4 cm to 7 cm in the vertical direction (measured from the chin towards the area above the upper lip). The height is preferably chosen so, that some facial movement and opening of the mouth is enabled. It has surprisingly be found, that the anti-snoring device (10) according to the present invention do even allow talking and coughing, which gives both a high comfort and a safety benefit.

The flexible sheet comprised by the anti-snoring device (10) according to the present invention should be selected to have a certain degree of flexibility. The flexibility provides for better conformation to the individual facial contours of a wearer, low stress on the adhesive areas during facial movement and convenient packaging of the device and should be selected in view thereof.

However, the flexible sheet comprised by the anti-snoring device (10) should also be selected to have a certain degree of rigidness. Depending on the particular embodiment of the present invention, the rigidity of the flexible sheet prevents that the sheet extends into the mouth of the wearer (if open). Contact of the tongue with this sheet may be considered as unpleasant by some wearer, for example since the taste of a non-woven material may be experienced as unpleasant.

In some embodiments according to the present invention the entire wearer facing side (12) of the anti-snoring device (10) may be covered with an adhesive as disclosed herein. This allows for simple production processes, for example can the device than be cut out from a larger uniform sheet of material. This also allows for a very high freedom for the application of the device with regard to position and orientation.

In other embodiments of the present invention the adhesive on the wearer facing side (12) of the anti-snoring device (10) can be applied in any pattern, symmetrical or unsymmetrically, e.g. a pattern of dots or stripes.

In yet further and highly preferred embodiments of the present invention the mouth portion (16) of the wearer facing side (12) of the anti-snoring device (10) is adhesive free. This avoids tongue contact with the adhesive which can be assumed to be unpleasant and may even lead to difficulties in removing the tongue from the mouth portion (16). In a further aspect, this allows to save adhesive and is hence associated with economical and environmental benefits. In yet a further aspects the adhesive free mouth portion helps in the application of the device as it avoids pre-mature and unintended sticking of the device. Moreover an adhesive may often impart a stiffness to the flexible sheet with may not be wanted of the reasons outlined above.

While an adhesive free mouth portion can be surrounded by a continuous peripheral strip of adhesive, in a highly preferred embodiment of the present invention the peripheral portion (18) is provided with a discontinuous application of adhesive. In such embodiment the peripheral portion (18) comprises adhesive coated (20) and adhesive free areas (22). The provision of adhesive free areas (22) in the peripheral portion (18) is associated with the benefits mentioned above for the adhesive free mouth portion (16). While adhesive free areas (22) are preferred a discontinuous application of adhesive should also be achieved by applying different adhesives, namely adhesive of different strength, or by inactivating portions of an adhesive (e.g. by covering with a non-adhesive material).

A further benefit of adhesive free portions in the mouth portion (16) and in particular in the peripheral portion (18) is that an anti-snoring device (10) can be provided which comfortably fits a variety of people and hence lends itself to a "one size fits all"-concept. In particular if a continuous strip of adhesive is present on the peripheral portion (18), the anti-snoring device (10) must be provided as to fit the wearer rather accurately, as to not stick e.g. to the lips, the nose. For such a "one size fits all"-concept it is particularly beneficial, to combine the above described adhesive application with a rather flexible sheet.

Preferably the adhesive free portions in the mouth portion (16) should have a total surface area of at least 1 cm$^2$, preferably 3 cm$^2$, more preferably 5 cm$^2$. Preferably the total adhesive free surface area in the mouth portion (16) measures at least 10%, preferably at least 25%, more preferably at least 50% of the total surface area of the wearer facing side (12) of the anti-snoring device (10).

Preferably the adhesive coated portions (20) on the wearer facing side (12) of the flexible sheet should have a total surface area of less than 10 cm$^2$, preferably less than 5 cm$^2$, more preferably less than 2 cm$^2$. Preferably the total adhesive coated surface area measures less than 50%, preferably less than 25%, more preferably less than 10%, yet more preferably less than 5% of the total surface area of the wearer facing side (12) of the anti-snoring device (10).

Preferred anti-snoring device (10) comprise a release sheet, e.g. a release paper, covering at least the adhesive coated areas (20) of the anti-snoring device (10). Further may the anti-snoring device (10) be provided with lobes to allow for easier detachment of the device. Where sufficient adhesive free areas are provided on the wearer facing side (12) the provision of dedicated lobes may be redundant.

One preferred embodiment of the present invention is shown in FIG. 1. In this embodiment the peripheral portion (18) of the wearer facing side (12) of the anti-snoring device (10) comprises four distinct adhesive coated areas (20). Any even or uneven number of adhesive coated areas (20) may be present, two, four, six or eight being preferred.

Another preferred embodiment of the present invention is shown in FIG. 2. In this embodiment the peripheral portion (18) of the wearer facing side (12) of the anti-snoring device (10) comprises two strips of adhesive. Preferably such strips have a width from 1 mm to 20 mm, more preferably 5 mm to 10 mm. Preferably the strips have a distance from 5 mm to 50 mm, more preferably 10 mm to 30 mm to provide an adhesive free mouth portion (16) in-between. Any even or uneven number of stripes may be present, two or four strips being preferred. The strips may have any orientation, a vertical orientation being preferred and a horizontal orientation being even more preferred. The strips may also not be provided from the same adhesive, e.g. to account for different levels of sebum encountered in different facial areas.

Preferred Adhesives for the Anti-Snoring Device

The adhesive is provided in one or several areas on the wearer facing side (12) of the anti-snoring device (10) as a layer having a certain thickness or calliper C measured in millimeters (mm). Preferably the calliper C is constant for all adhesive coated areas (20), but the calliper C may also vary.

The adhesive is applied on at least portion of the wearer facing surface of devices in a layer having a thickness or caliper that is preferably constant, or that alternatively can vary over the surface interested by the application of the adhesive. The adhesive can be applied to the wearer facing surface of the device by any means known in the art such as slot coating, spiral or bead application or printing. Typically the adhesive is applied at a basis weight of from 20 g/m² to 2500 g/m², preferably from 500 g/m² to 2000 g/m², most preferably from 700 g/m² to 1500 g/m² depending in the end use envisioned.

Detailed analysis of the sequence of common situations occurring from the application of anti-snoring devices (10) to the time of removal of such devices has shown that specific adhesive characteristics need to be preferably satisfied in order to achieve the desired performance objectives, in particular to secure initial attachment, secure attachment during use and painless removal after wear. The characteristics which have been considered in this context are the elastic modulus describing the elastic behaviour of the material and the viscous modulus which describes the viscous behaviour of the adhesive material.

The viscous behaviour of the adhesive can be interpreted to represent an indication of the ability of the adhesive to quickly attach and securely adhere to a particular surface. The elastic behaviour can be interpreted as an indication of the "hardness" behaviour of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

In order to provide adhesives for secure initial and prolonged attachment and easy/painless removal the relation between the elastic modulus and the viscous modulus as well as their dynamic behaviour is also of importance.

The adhesive has an elastic modulus at a temperature of 37° C. (100° Fahrenheit) abbreviated $G'_{37}$, a viscous modulus at a temperature of 37° C. (100° Fahrenheit) of $G''_{37}$, and a viscous modulus at a temperature of 25° C. (77° Fahrenheit) of $G''_{25}$.

The adhesive according to the present invention preferably satisfies the following conditions;

| | |
|---|---|
| $G'_{37}$ (1 rad/sec) | is in the range 500 Pa to 20000 Pa, preferably 700 Pa to 15000 Pa, most preferably 1000 Pa to 10000 Pa. |
| $G''_{37}$ (1 rad/sec) | is in the range 100 Pa to 15000 Pa, preferably 100 Pa to 10000 Pa, most preferably 300 Pa to 5000 Pa. |
| and the ratio of $G''_{37}$ (1 rad/sec)/$G''_{37}$ (1 rad/sec) | is in the range of 1 to 30. |

Provided the above Theological conditions are satisfied the adhesives will also satisfy conditions such as sufficient cohesiveness (to prevent residue of adhesive on the skin) which are important for commercial use of such adhesives and apparent to those skilled in the art. Adhesive compositions which satisfy the above criteria can be used as adhesives for the device provided they also satisfy the common requirements of being safe for use on human or animal skin during use and generally after disposal of the device.

Often the criteria of hygienic appearance such that adhesive compositions which are transparent or white upon application are preferred.

It has been determined that the relation between the thickness or calliper C, measured in millimeters (mm), of the layer in which the adhesive is provided, typically onto at least a portion of the wearer facing surface of the device, and the viscous modulus $G''_{25}$ at about 100 rad/sec of the adhesive, is relevant to the scope of providing an easy and painless removal from the wearer's skin of such a adhesive applied on at least a portion of the wearer facing surface of an device for attachment of said device to the skin of a wearer.

The adhesive of the present invention is thus preferably provided as a layer having a thickness C such that the viscous modulus $G''_{25}$ (100 rad/sec) and the thickness C preferably satisfy the following empirical equation:

$$G''_{25} \leq [(7.00+C) \times 3000] \text{Pa}$$

and preferably also the following empirical equation:

$$G''_{25} \leq [(5.50+C) \times 1700] \text{Pa}$$

While in a preferred embodiment of the present invention the thickness C of the adhesive layer is constant, such an adhesive layer can also have different thicknesses in different portions of the wearer facing surface of the device where it is applied, provided that the above mentioned relationship between C and $G''_{25}$ is in any case satisfied in each portion.

The skin of the wearer to which the devices are typically applied will vary considerably from person to person. In particular the type and amount of grease or sebum produced can vary considerably from person to person. However, the facial area, and in particular around the chin, is generally known to produce high levels of sebum and to quickly reproduce such sebum, even if some is removed, e.g. by cleaning of the pertinent skin areas. Moreover, the wearers of such devices may apply creams to the area of skin which will contact the adhesives, e.g. moisturing creams. It is thus important to provide an adhesive which adheres to greasy skin. Accordingly the present invention provides an adhesive having a dry initial peel strength ($P_{DI}$) and a greasy initial peel strength ($P_{GI}$) as determined by the test method described herein, where the ratio $P_{DI}$ to $P_{GI}$ is from 1:1 to 1.0:0.2, preferably from 1:1 to 1:0.3. Typically for utilisation for devices the dry initial peel strength is ($P_{DI}$) is from 0.1 N/cm to 7.0 N/cm, preferably from 0.1 N/cm to 5.0 N/cm, more preferably from 0.5 N/cm to 3 N/cm. The value of the grease initial peel strength is preferably the same as for the dry initial peel strength. However typically a lower level is achieved and is acceptable at levels from 0.1 N/cm to 5 N/cm, preferably from 0.1 N/cm to 3 N/cm, more preferably from 0.1 N/cm to 2 N/cm. It is also preferable that the adhesion to greasy skin is maintained over a period of wear time such that the ratio between the greasy initial peel strength ($P_{GI}$) and the greasy final peel strength ($P_{GF}$) is from 1:1 to 1:0.25 preferably from 1:1 to 1:0.5.

Due to the nature and environment in which such devices are utilised it is also preferably a feature that the adhesive has a water absorption capacity as defined in the test herein of at least 3% by weight of said adhesive (so that the adhesive adheres directly onto wet or moist skin). In particular, the ratio of the peel strength of the adhesive as determined in the test methods herein should most preferably be maintained at a constant value such that the ratio of initial peel strength ($P_{DI}$) and the final peel strength ($P_{WF}$) is from 2:1 to 1:4, preferably from 2:1.25 to 2:4, most preferably from 2.0:1.5 to 2.0:2.5. Typically for devices the initial peel strength for dry and more preferably also for wet skin should be from 0:1 N/cm to 7.0 N/cm, 0.1 N/cm to 5.0 N/cm, preferably from 0.5 N/cm to 3.0 N/cm.

It is further also preferable that the adhesive in addition to maintaining its peel strength over a period of time even in the presence of water also absorbs less than 15%, preferably less than 10%, more preferably less than 7% water. Whilst not intending to being bound by theory, it is believed that in order to obtain direct adhesion onto wet skin and maintain constant adhesion performance over a period of wear, even when exposed to excess liquids or high humidity the ability of the adhesive to absorb water needs to be considered. In particular, it has been identified that, not only the absolute ability of the adhesive needs to be considered, but also the rate of water absorption in order to provide an adhesive meeting the above identified performance parameters.

For example hydrocolloid particle containing adhesives which are known in the art comprising a 3-dimensional rubber matrix and colloidal absorbent particles dispersed therein are only able to absorb limited amounts of water through the colloidal particles themselves and not the matrix itself. In addition the rate at which water is absorbent is slow. Hence these prior art adhesives do not adhere to wet surfaces.

Prior art hydrogel adhesives on the other hand are able to not only absorb large quantities of water but also at a very fast rate. As a result such adhesives may be able to adhere, to wet surfaces, however due to the combination of fast rate of absorption and large absolute water uptake, these adhesives loose their adhesive strength rapidly in the presence of excess water or high humidity.

Accordingly the adhesives of the present invention exhibit both an ability to adhere directly to wet skin, by having a minimum absolute water absorption ability in combination with a rate of absorption such that the peel strength remains within defined levels over the period of wear.

The adhesive is provided with the preferred pattern, typically on the wearer facing surface of the device, as a layer having a thickness or calliper C that is preferably constant. The layer can be preferably continuous or alternatively discontinuous, e.g. in form of dots, spirals, or stripes.

Even though adhesives are used like pressure sensitive adhesives on human skin hair and mucous tissues, it is understood that the adhesive compositions could only with difficulty be considered typical pressure sensitive adhesives (referred to as PSA hereinafter) on the basis of the most characteristic rheological behaviours identifying such materials.

In fact as the person skilled in the art of adhesives knows, the most characteristic feature that distinguishes a PSA from other substances that can temporarily adhere objects (e.g. water between two glass plates could) is the fact that their rheological parameters and especially the Elastic Modulus G' vary greatly with the frequency of applied stresses. More in particular, G' of PSA can increase over some orders of magnitude, while the frequency of applied stresses varies from typical bonding frequency to typical debonding frequency, i.e. 1 rad/s to 100 rad/s as indicated below.

As a first consequence, it is therefore inadmissible to define materials intended for use as "adhesives" by giving values of rheological parameters and especially of G' at a fixed value of frequency. This can be misleading because in the absence of other characteristics such as surface chemistry it will include materials which have no practical value. It is hence necessary that rheological characterisation must be on the basis of dynamic considerations. This not only applies to the Elastic Modulus G' but also to the viscous modulus G" and hence also for tan (d)=G"/G'.

It is well known that typical PSAs have not only a high variation of G' across the considered frequencies, but also that there is an even higher variation of G" which can get close or become even higher than the value of G', i.e. tan (d) becomes about or even greater than 1, in particular at the frequencies that are typical of debonding.

Without wishing to be bound by theory this can be interpreted as meaning that a high fraction of the energy applied for the debonding is dissipated within the adhesive (so it is not effective in causing the debonding) and through the interface of the adhesive and the skin, while this fact causes macroscopically the recording of a very high level of adhesive force.

As indicated above materials useful as adhesives according to the present invention have rheological characteristics which are measured at a reference temperature of 37° C. (as usual body temperature of humans) and in a range of frequencies. It has been found that upon application of an device with a adhesive the adhesive contact is formed at a low frequency, while debonding happens at the speed of removing the device. This speed is expressed as a frequency of 100 rad/s, while the low frequency of forming the adhesive bond has been found to be on the order of 1 rad/s. Therefore, the frequency range for use according to the present invention is between 1 and 100 rad/s.

In order to provide good conditions of bonding, i.e. at a frequency of about 1 rad/sec, the absolute values of the elastic modulus should not be too high, otherwise the adhesive is too hard and it is not able to intimately join or mold to the surface to which it is expected to adhere. It is also important to have a low absolute value of G" in order to have good cohesion while the material remains soft and capable of gently adhering to skin.

The ratio of $G'_{37}$ (1 rad/sec) over $G''_{37}$ (1 rad/sec) is important to ensure that these two values are balanced upon adhesion to the skin.

Importantly, the ratio of $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

needs to be large enough to ensure that the dynamic behaviour of both the elastic and the viscous module are maintained in a relationship which provides secure adhesion and painless and easy removal.

Finally the person skilled in the art will also recognise that the Glass Transition Temperature Tg of the adhesive composition, the specific heat capacity, and the specific heat conductivity are parameters which are useful to more fully define the group of useful adhesives.

The following set of characteristics should preferably be satisfied for the adhesive of the present invention:
the ratio $$\frac{G'_{37}(100 \text{ rad/sec}) - G''_{37}(100 \text{ rad/sec})}{G'_{37}(1 \text{ rad/sec}) - G''_{37}(1 \text{ rad/sec})}$$

is not less than 0.5, preferably in the range 0.7 to 3, most preferably in the range 1 to 1.8.

The value of the ratio of $G'_{37}/G''_{37}$ at least for the frequency range above 1 rads/up to 100 rads/s should preferably be not less than 0.5, preferably from 0.7 to 10 and most preferably from 1 to 7.

The rheological behaviour can also be related to the values of the Glass Transition Temperature Tg. For topical adhesives according to the present invention Tg should preferably be less than 0° C., more preferably less than −5° C. and most preferably less than −10.

In order to provide adhesive compositions which satisfy the requirements of the above rheological and physical characteristics of an adhesive any medically suitable substantially water insoluble pressure sensitive adhesives comprising a polymer which forms a 3-dimensional matrix meeting the these characteristics may be utilised.

According to the present invention the 3-dimensional matrix also referred to herein as a gel, comprises as an essential component a polymer which can be physically or chemically cross linked. The polymer may be naturally or synthetically derived. The uncrosslinked polymer includes repeating units or monomers derived from vinyl alcohols, vinyl ethers and their copolymers, carboxy vinyl monomer, vinyl ester monomers, esters of carboxy vinyl monomers, vinyl amide monomers, hydroxy vinyl monomers, cationic vinyl monomers containing amines or quaternary groups, N-vinyl lactam monomer, polyethylene oxides, polyvinylpyrrolidone (PVP), polyurethanes, acrylics such as methyl acrylate, 2-hydroxyethyl methacrylate, methoxydiethoxyethyl methacrylate and hydroxydiethoxyethyl methacrylate, acrylamides, and sulphonated polymers such as acrylamide sulphonated polymers for example 2 acrylamido methylpropane sulphonic acid (AMPs) and acrylic (3-sulphopropyl) ester acid (SPA), and mixtures thereof. Also acrylonitrile, methacrylamide, N,N,-dimethylacrylamide (NNDMA), acrylic esters such as methyl, ethyl and butyl acrylates. Alternatively, the uncrosslinked polymer may be a homopolymer or copolymer of a polyvinyl ether, or a copolymer derived from a half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade styrol/ethylene-butylene/styrol (SEBS), styrene/isoprene/styrene (SIS), and styrol/ethylene-propylene/styrol (SEPS).

Particularly preferred polymers are acrylics, sulphonated polymers such as acrylamide sulphonated polymers, vinyl alcohols, vinyl pyrrolidone, polyethylene oxide and mixtures thereof. Most preferred are nitrogen containing polymers.

According to the present invention the 3-dimensional adhesive matrix also essentially comprises a plasticiser, which is preferably a liquid at room temperature. This material is selected such that the polymer may be solubilized or dispersed within the plasticiser. For embodiments wherein irradiation cross linking is to be carried out, the plasticiser must- also be irradiation cross linking compatible such that it does not inhibit the irradiation cross linking process of the polymer. The plasticiser may be hydrophilic or hydrophobic.

Suitable plasticisers include water, alcohols, polyhydric alcohols such as glycerol and sorbitol, and glycols and ether glycols such as mono- or diethers of polyalkylene gylcol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such phthalates, adipates, stearates, palmitates, sebacates, or myristates, and combinations thereof. Particularly preferred are polyhydric alcohols, polyethylene glycol (with a molecular weight up to about 600), glycerol, sorbitol, water and mixtures thereof.

Typically the adhesive comprises a ratio of polymer to plasticiser by weight of from 1:100 to 100:1, more preferably from 50:1 to 1:50. However, the exact amounts and ratios of the polymer and plasticiser will depend to a large extent on the exact nature of polymer and plasticisers utilised and can be readily selected by the skilled person in the art. For example a high molecular weight polymer material will require a greater amount of plasticiser than a low molecular weight polymer.

In addition, the adhesive also further preferably comprises a lipid-micellising polymer, i.e. a so-called hypercoiling polymer. This polymer functions to micellise and remove the rolled up pockets of grease from the gel-skin interface.

This hypercoiling polymer has the capability of more effectively solvating the primary surfactant micelles that contact hydrophobic skin contaminant such as skin lipid or skin creme. The consequence of this functional role is that the work of adhesion between adhesive and skin is progressively less affected by the presence of either or both surfactant or hydrophobic skin contaminant.

The hypercoiling polymer preferably comprises any of the following, either alone or in combination: poly (maleic acid styrene), poly (maleic acid butyl vinyl ether), poly (maleic acid propyl vinyl ether), poly (maleic acid ethyl vinyl ether) and poly (acrylic acid ethyl acrylate).

A particularly preferred example is an alternating copolymer of styrene and maleic anhydride. As discussed herein after the adhesive seeks to provide a biphasic structure on polymerisation. These two phases are hydrophilic and hydrophobic. The hydrophobic phase my be provided by a hydrophobic monomer which is initially maintained as part of the homogenous reaction mixture by way of a reactive solvent bridge. Alternatively and/or additionally the hydrophobic component is provided as a polymer which separates from the aqueous phase on polymerisation.

The exact amounts and ratios of the hypercoiling polymer will depend to a large extent on the nature of the components.

In certain circumstances the reaction mixture preferably comprises from 3% to 20%, and more preferably from 8% to 18% by weight of the reaction mixture, of a stabilised polymer dispersion that is used to provide a stable phase separated system. The polymer preferably comprises any of the following either alone or in combination: vinylacetate dioctyl maleate copolymer or ethylene-vinyl acetate copolymer. Ethylene-vinylacetate copolymer is preferred, such as that marketed under the trade name DM137 by Harlow Chemicals.

The adhesive also preferably comprise surfactants such as nonionic, cationic, anionic, amphoteric and any mixtures thereof.

Suitable nonreactive nonionic surfactants include but are not limited to those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles and most preferably about 5 to about 20 moles of ethylene oxide. Examples of such nonionic ethoxylated fatty alcohol surfactants are the Tergitol.™. 15-S series from Union. Carbide and Brij.™. surfactants from ICI. Tergitol.™. 15-S Surfactants include $C_{11}$–$C_{15}$ secondary alcohol polyethyleneglycol ethers. Brij.™ 58 Surfactant is Polyoxyethylene(20) cetyl ether, and Brij.™.76 Surfactant is Polyoxyethylene(10) stearyl ether.

Other suitable nonreactive nonionic surfactants include but are not limited to those selected from the group consisting of the polyethylene oxide condensates of one mole of alkyl phenol containing from about 6 to 12 carbon atoms in a straight or branched chain configuration, with about 3 to about 100 moles of ethylene oxide. Examples of nonionic surfactants are the Igepal.™. CO and CA series from Rhone-Poulenc. Igepal.™. CO surfactants include nonylphenoxy poly(ethyleneoxy) ethanols. Igepal.™. CA surfactants include octylphenoxy poly(ethyloneoxy) ethanols.

Another group of usable nonreactive nonionic surfactants include but are not limited to those selected from the group consisting of block copolymers of ethylene oxide and propylene oxide or butylene oxide.

Examples of such nonionic block copolymer surfactants are the Pluronic.™. and Tetronic ™. Series of surfactants from BASF. Pluronic.™. surfactants include ethylene oxide-propylene oxide block copolymers. Tetronic.™. surfactants include ethylene oxide-propylene oxide block copolymers. Suitable examples are Pluronic L68 and Tetronic 1307. Particularly suitable examples are Pluronic L64 and Tetronic 1107.

Still other satisfactory nonreactive nonionic surfactants include but are not limited to those selected from the group consisting of sorbitan fatty acid esters, polyoxyethylene sorbitan fatty acid esters and polyoxyethylene stearates. Examples of such fatty acid ester nonionic surfactants are the Span.™., Tween.™., and Myrj.™. surfactants from ICI. Span.™. surfactants include $C_{12}$–$C_{18}$ sorbitan monoesters. Tween.™. surfactants include poly(ethylene oxide) $C_{12}$–$C_{18}$ sorbitan monoesters. Myrj.™. surfactants include poly(ethylene oxide) stearates.

Suitable anionic surfactants will normally include a hydrophobic moiety selected from the group consisting of (about $C_6$ to about $C_{20}$) alkyl, alkylaryl, and alkenyl groups and an anionic group selected from the group consisting of sulfate, sulfonate, phophate, polyoxyethylene sulfate, polyoxyethylene sulfonate, polyoxyethylene phosphate and the alkali metal salts, ammonium salts, and tertiary amino salts of such anionic groups.

Anionic surfactants which can be used in the present invention include but are not limited to those selected from the group consisting of (about $C_6$ to about $C_{20}$) alkyl or alkylaryl sulfates or sulfonates such as sodium lauryl sulfate (commercially available as Polystep.™ B-3 from Srepan Co.) and sodium dodecyl benzene sulfonate, (commercially available as Siponate.™.DS-10 from Rhone-Poulene); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep.™.B-1 commercially available from Stepan Co. and Alipal.™.EP110 and 115 from Rhone-Poulenc; (about $C_6$ to about $C_{20}$) alkyl or alkylphenoxy poly(ethyleneoxy)ethyl mono-esters and di-esters of phosphoric acid and its salts, with the ethylene oxide repeating unit in the surfactant below about 30 units, preferably below about 20 units, most preferably below about 15 units, such as Gafac.™.RE-510 and Gafac.™.RE-610 from GAF.

Cationic surfactants useful in the present invention include but are not limited to those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One ore more of the substituents may include an aryl moiety or may be replaced by an aryl, such as benzyl or phenyl.

In a particularly preferred embodiment of the invention the surfactant comprises at least one propylene oxide/ethylene oxide block copolymer, for example such as that supplied by BASF Plc under the trade name Pluronic L64. The reaction mixture ideally comprises from 0.1% to 5%, by weight of the reaction mixture, of surfactant.

The surfactant acts to remove the grease from the skin and to form the removed grease into isolated pockets within the hydrogel without reducing the work of adhesion of the coating.

Other common additives known in the art such as preservatives, antioxidants, pigments, mineral fillers and mixtures thereof may also be comprised within the adhesive composition in quantities up to 10% by weight each respectively.

According to the present invention the polymer component of the adhesive can be physically or chemically cross linked in order to form the 3-dimensional matrix. Physical cross linking refers to polymers having cross links which are not chemical covalent bonds but are of a physical nature such that there are areas in the 3-dimensional matrix having high crystallinity or areas having a high glass transition temperature. Chemical cross linking refers to polymers which are linked by chemical bonds. Preferably the polymer is chemically cross linked by radiation techniques such as thermal-, E beam-, UV-, gamma or micro-wave radiation.

In addition when chemical crosslinks are formed in the system, a polyfunctional cross linker and/or a free radical initiator may be present in the premix to initiate the crosslinking upon irradiation. Such an initiator can be present in quantities up to 5% by weight, preferably from 0.02% to 2%, more preferably from 0.02% to 0.2%. Suitable photoinitiators include type I-α-hydroxy-ketones and benzilidimethyl-ketals e.g. Irgacure 651 which are believed to on irradiation to form benzoyl radicals that initiate polymerization. Photoinitiators of this type that are preferred do not carry any subtitients in the para position of the aromatic ring. Particularly preferred is I-hydroxycyclohexylphenylketone (available under the trade name Irgacure 184 from Ciba Speciality Chemicals), also preferred are Darocur 1173 (2-hydroxy-2-propylphenyl ketone) and mixtures of Irgacure 184 and Darocur 1173. In addition from 0.02% to 2% of thermal initiators may also be used.

The resulting adhesive composition is mainly hydrophilic. Hydrophobic and mixed phase compositions are dependant upon the nature of the components of the adhesive. In addition a mixture of monomers whether hydrophilic or both hydrophilic and hydrophobic may result in a single phase or mixed phase of at least 2 phases. Preferably, the adhesives of the present invention are mixed phase hydrophilic hydrophobic.

A mixture of monomers which may result in 1, 2 or more phases are preferred. Mixed phase adhesives are compositions in which both hydrophobic and hydrophilic components, preferably in both plasticisers and polymers, form two or more separate phases. In such cases an emulsifier is preferably present at a suitable level to form stable emulsions between the incompatible phases.

Whilst not intending to be bound by theory it is believed that the improved peel strength liquid stability particularly with respect to water of the adhesives is obtained from a monomer mix comprising both hydrophilic e.g. polar and/or ionic monomers preferably an ionic water soluble monomer and hydrophobic i.e water insoluble monomers. Preferably the ratio of hydrophilic monomers to hydrophobic monomers should be in the range of from 5:1 to 1:5, preferably from 3:1 to 1:3, more preferably from 2:1 to 1:2. The hydrophilicity and hydrophobicity of a monomer component is always relative to the other component. Typically prior art hydrogel adhesives comprise hydrophilic monomers only, as a consequence of which they have a high rate of water absorption and do not maintain adhesion after exposure to excess liquid. Whilst not intending to be bound by theory, it is believed that the presence of a hydrophobic component in the adhesive matrix reduces the rate of absorption of water of the adhesive. As a result the distribution of the water absorbed by the adhesive is more uniform. Consequently a water film is not generated between the surface of the skin and the adhesive, which if present, prevents the formation of bonds between skin and adhesive and thus the adhesive capacity of the adhesive itself.

Thus the invention seeks to provide a homogeneously dispersed reaction mixture comprising both hydrophobic and hydrophilic components which, on polymerisation separates into a biphasic or a multiphasic structure. The phases have in some cases been observed to have a thickness of about 100 microns+/−50 microns. The reaction mixture may contain one or more surface active agents which may assist or promote phase separation but in the course of polymersation become anistropically distributed between the result phases.

The presence of a hydrophobic monomer or polymer may be necessary in the initial homogenous dispersion in order to more effectively promote phase separation.

It is a consequence of this invention that the phase separated material contains relatively hydrophobic regions, which enable the polymer to function as a pressure sensitive adhesive, and substantially hydrophilic region, which enable the surface active agent to function in an aqueous environment at the interface between the polymer and mammalian skin. When the polymer is placed in contact with skin, the nature and quantity or surface active agent are chosen to bring about the removal of natural or synthetic hydrophobic material, such as skin lipid or skin creme, from the skin surface without adversely diminishing the work of adhesion between the hydrophobic domains and the skin surface. In as much as both the polymeric adhesive formed in this invention and the skin with which it is contacted are deformable under conditions of normal use, an equilibrium interfacial situation is reached in which some spatial exchange of hydrophobic regions and hydrophobic regions will have taken place on the skin surface.

Suitable preferred hydrophilic monomers are acrylic acid, and salts thereof, 2-acrylamido methylpropane sulphonic acid, acrylic (3-sulphopropyl) ester acid and salts thereof and combinations thereof. A particularly preferred example is 2-acrylamide-2-methylpropane sulphonic acid sodium salt commonly known as NaAMPs available commercially from Lubrizol as either a 50% aqueous solution (reference code LZ 2405) or at a 58% solution (refernce code LZ 2405 A). Suitable hydrophobic monomer components are methyl-, ethyl-, n-butyl, hexyl, iso octyl- and isodecyl acrylates and methacrylate, vinyl ethers, vinyl pyrrolidine, gylcidyl acrylate and ethoxy ethyl acrylate, tehra-hydrofurfuryl acrylate, hydroxypropyl acrylate, vinyl propionate and vinyl butyrate, and combinations thereof. Particularly preferred are ethoxy ethyl acrylate or butyl acrylate.

When the adhesive comprises a hydrophobic component, such as butyl acrylate as well as a hydrophilic monomer (i.e. the aforesaid water soluble ionic monomer), such as NaAMPS, the presence of a nonionic water soluble monomer, for example NNDMA is preferred to act as a so-called "reactive solvent bridge" to provide intimate mixing of the various seemingly incompatible components of the reaction mixture- prior to polymerisation. The reaction mixture thus has a homogenous structure containing both hydrophilic and hydrophobic components that are intimately mixed, as the NNDMA acts as a solvent for both hydrophilic and hydrophobic materials, providing a clear compatible coating solution or dispersion. As the reactive solvent bridge is polymerised and thus essentially removed from the reaction mixture the stability of the system is adversely affected and the compatible coating solutions or dispersions undergo phase separation so as to provide a biphasic structure.

In a preferred embodiment of the invention the aforesaid non ionic water soluble monomer will comprise at least one of a mono- or di-N-alkylacrylamide or an analogue thereof. The term "analogue" in this context refers to non ionic water soluble monomers containing an alkyl or substituted alkyl group linked to a carbon-carbon double bond via an amido or alkylamido (—CO.NH— or CO.NR—) function. Examples of such analogues include diacetone acrylamide (N-1,1-dimethyl-3-oxobutyl-acrylamide), N-alkylated acrylamides, N,N-dialkylated acrylamides, N-vinyl pyrrolidone and acryloyl morpholine. N,N-dimethylacrylamide (NNDMA) and/or and analogue thereof is preferred. The reaction mixture preferably comprises from about 15% to about 30% and ideally from about 15% to about 25%, by weight of the reaction mixture, of the non ionic water soluble monomer.

The term "reactive solvent bridge" used herein refers to a partially lipophilic non ionic water soluble monomer which has the ability to partition between the hydrophobic and aqueous phases, whereby the hydrophobic monomer is substantially solubilised in the homogeneous reaction mixture before polymerisation begins. The solvent bridge is reactive in that it is a polymerisable monomer which takes part in the polymerisation reaction. Without wishing to be bound by theory, it is believed that the solvent bridge function of the non ionic water soluble monomer is exercised predominantly prior to, and in the relatively early stages of, the polymerisation reaction, and reduces as the polymerisation reaction proceeds.

In preparing adhesive compositions in accordance with the invention, the ingredients will usually be mixed to provide a homogeneous reaction mixture in the form of an initial pre-gel aqueous based liquid formulation, and this is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid substrate. The incident UV intensity, at a wavelength in the range from 240 to 420 nm, is ideally substantially 40 mW/cm$^2$. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers and for conversion better than 99.95% exposure to UV light less than 60 seconds and preferably less than 40 seconds is preferred. Those skilled in the art will appreciate that the extent of irradiation will be dependent on the thickness of the reaction mixture, concentration of photoinitiator and nature of substrate on to which the reaction mixture is coated and the source of UV.

These timings are for medium pressure mercury arc lamps as the source of UV operating at 100 W/cm. The intensity of UV @ 254 nm and 313 nm reaching the surface of the substrate is approximately 150 μW/cm$^2$ and 750 μW/cm$^2$. For a given lamp UV intensity in a function of the operating power and distance of the reaction mixture from the UV source.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes. Preferably the conversion of the hydrophilic monomers present such as NaAMPS should be 98%, preferably 99% most preferably 99.9% so that the amount of monomer within the adhesive is 4600 microg/g or less, preferably 2300 microg/g or less, most preferably 230 microg/g or less. Similarly, the conversion of the hydrophobic monomers present such as NNDMA should be 99%, preferably 99.9%, most preferably 99.99% so that the amount of monomer present in the adhesive is 2200 microg/g or less, preferably 220 microg/g or less, more preferably 22 microg/g or less.

The adhesive is thus typically formed by polymerising a homogeneous aqueous reaction mixture comprising from 5 to 50%, preferably from 30% to 50% by weight of the reaction mixture, of hydrophilic monomer, i.e. an ionic water soluble monomer, from 10% to 50%, preferably from 15% to 45% by weight of the reaction mixture, of a plasticiser (other than water), up to 50%, preferably from 10% to 50%, more preferably from 15% to 30% most preferably from 15% to 25% by weight of the reaction mixture, of a nonionic, water soluble monomer, from up to 40%, preferably from 0.05% to 40%, more preferably from 3 to 40%, by weight of the reaction mixture, of water. If present the reaction mixture comprises from up to 10%, preferably from 0.05% to 9%, more preferably less than 8% by weight of the reaction mixture, of a surfactant. Similarly the reaction mixture may also comprise from 0.1% to 5%, by weight of the reaction mixture, of a lipid micelling polymer, and may comprise from 1% to 30% by weight of the reaction mixture of at least one hydrophobic monomer.

The term "homogeneous aqueous reaction mixture" used herein refers to a substantially solubilised system in which substantially no phase segregation occurs prior to the polymerisation reaction. For example, an emulsion, microemulsion or phase-separated mixture in which a polymerisation reaction later occurs is not a homogeneous aqueous reaction mixture as understood for the purpose of the present invention. Where a reaction mixture includes hydrophobic components, special measures will therefore be required, to achieve homogeneity, as described in more detail herein.

Surface Characteristics of the Polymerised Materials

It is a consequence of this invention that the phase separated polymerised material contains at least at its surface relatively hydrophobic regions, which enable the polymer to function as a pressure sensitive adhesive, and substantially hydrophilic regions, which enable the surface active agent to function in an aqueous environment at the interface between the polymer and mammalian skin. When the polymer is placed in contact with skin, the nature and quantity of surface active agent are chosen to bring about the removal of natural or synthetic hydrophobic material, such as skin lipid or skin creme, from the skin surface without adversely diminishing the work of adhesion between the hydrophobic domains and the skin surface. In as much as both the polymeric adhesive formed in this invention and the skin with which it is contacted are deformable under conditions of normal use, an equilibrium interfacial situation is reached in which some spatial exchange of hydrophobic regions and hydrophobic regions will take place on the skin surface.

The phase separated polymerised surface material is found to include predominantly well defined hydrophobic phases embedded in a hydrophilic matrix in which the water is predominantly contained. The hydrophobic phases are generally of elongated form, with a transverse dimension above the wavelength of light (e.g. about 0.5 to about 100 microns). They may therefore be visualised under a light microscope on a sample stained with a dye which binds preferentially to the hydrophobic phase.

The surface morphology of the elongate hydrophobic phases can vary widely. Without wishing to the bound by theory, it is believed that variations in the surface tension at the hydrophobic/hydrophilic interface as the polymerisation reaction proceeds can cause the morphologies to vary in the final polymer. This surface tension can be affected by the nature and amount of both the reactive solvent bridge and the surfactant, and by other factors.

Thus, it is possible for the elongate hydrophobic phases at the surface of the polymerised material to congregate in a clustered, or alternatively a relatively open, arrangement. The hydrophobic phase visualised microscopically may, for example, appear as discontinuous linear and/or branched strands, or closed loops, embedded in the hydrophilic matrix.

The polymerised material is typically non-bicontinuous. At least one of the hydrophobic and hydrophilic phases exists as discrete regions within the polymerised material, and both phases do not simultaneously extend across the polymerised material (bicontinuity).

The adhesive is provided, typically on at least a portion of the wearer facing surface of the device, as a layer having a thickness or calliper C that is preferably constant, or that alternatively can vary over the surface of application of the adhesive.

When considering particularly the removal phase of an adhesive composition for attachment to the skin of a wearer, it is commonly recognised that good conditions of removal, i.e. at a frequency of about 100 rad/sec, of the adhesive applied to at least part of the wearer facing surface of the device, are achieved when the adhesive can be easily removed from the skin, and particularly from the bodily hair that may be located on this area of the skin, where the device contacts the body, without causing pain to the wearer, therefore without adhering too hard upon removal, to the skin and the hair of the wearer. Moreover, a good removal implies that the adhesive does not leave residues on the skin or on the hair.

The relationship between the thickness or calliper C measured in millimeters (mm) of the layer of the adhesive typically onto at least part of the wearer's facing surface of the device, and the viscous modulus $G''_{25}$ at 25° C. at about 100 rad/sec of the topical adhesive gives an indication of painless and easy removal of the adhesive from the skin.

Without being bound to any theory, it is believed that for higher values of $G''_{25}$ at 100 rad/sec, which overall correspond to a higher adhesiveness of the composition, a thicker calliper or thickness C of the adhesive layer is needed so that the energy applied for the removal is more evenly distributed within the mass of the adhesive, and is therefore transferred smoothly to the skin, so avoiding peaks of energy that typically cause the pain sensation to the wearer. In other words, thinner layers of the adhesive necessitate an adhesive with a lower $G''_{25}$ at 100 rad/sec to achieve a reduced pain sensation upon removal of the device.

Test Methods

Peel Adhesion Method

This is a quantitative method to determine the average peel force required to remove a skin at a specified peel angle and speed.

| Equipment | |
|---|---|
| Scissors | Convenient source |
| Standard ruler | Convenient source |
| Steel Roller | 5.0 kg Mass. 13 cm in diameter and 4.5 cm in width covered with 0.5 mm thick rubber. |
| Polyester Film | PET 23μ available from EFFEGIDI S.p.A., 43052 Colorno, Italy. |
| Transfer Adhesive | 3M 1524 available from 3M Italia S.p.a., 20090 Segrate Italy |
| Stop watch | Convenient source |
| Tensile Tester | Instron mod.: 6021 ( or equivalent) |

Test Procedure

| A) Tensile Tester Peel Settings: | |
|---|---|
| Load cell | 10 N |
| Test Speed | 1000 mm/min |
| Clamp to Clamp distance | 25 mm |
| Pre Loading | 0.2 N |
| Test Path "LM" | 50 mm |
| Measure variable | F average (N) in "LM" |

B) Skin Condition and Preparation

The sample is peel from the forearm. There are 3 conditions of the skin that are tested:
 1) Dry: The forearm is untreated and not wiped prior to test or between repetitions.
 2) Wet: To one cotton disk (Demak'up diameter 5.5 cm, weight about 0.6 g), 3 ml of distilled water is added. Next the disk is then wiped with a light pressure 3 times over the test area on the forearm. (The test area of the forearm is a rectangle approximately 2 cm wider and longer than the adhesive area).
 3) Greasy: To one cotton disk (Demak'up diameter 5.5 cm, weight about 0.6 g), 4 drops (about 0.2 g) of 'Nivea Body' are added. The disk is then folded in on itself to ensure the cream is absorbed. Next the disk is then wiped with a light pressure 3 times over the test area on the forearm. (The test area of the forearm is a rectangle approximately 2 cm wider and longer than the adhesive area).

C) Sample Preparation
 1. Allow the samples to adjust to conditioned room (23±2° Celsius and 50±2% RH) for about 1 hr.
 2. Prepare rectangular adhesive samples 260 mm±2 length and 20 mm±2 wide.
 3. Attach on the sample surface the polyester film (using the transfer adhesive to attach the polyester to the substrate surface).
 4. Each test specimen should be prepared individually and tested immediately.
 5. Remove the release paper from the adhesive without touching it. Attach one end to the skin (see section B).
 6. Roll the Steel Roller for 160 mm along the adhesive strip, once in each direction.

D) Test Environment
 There are 2 environments the adhesive can be tested in:
 1) Conditioned Room as described in C1.
 2) Wet Environment. Here, after step C4, the specimen is taken and put in a humidity controlled oven for 3 hours at 85 deg C. It is then taken out and steps C5, C6 are carried out.

E) Execution
1 minute after Step C6, take the free end of the specimen (approx. 100 mm long) and insert it in the upper end of the adhesion testing machine. Ensure the specimen is at a 90 degree angle to the forearm. Start the testing machine.

F) Report
Report the average of the peel strength of 5 tests. The single values are the base to calculate the standard deviation between the samples.

Residual Monomer Test Method

Test Sample
1 gram of a hydrogel sample is taken and emersed in 100 ml 0.9% saline water.
The sample is left in the saline at 40 deg C. for 24 hours.
An aliquot of the liquid is diluted and analysed by electrospray LC/MS/MS.
Calibration Sample
1 gram of reference monomers (eg NaAmps) are dissolved in 100 ml 0.9% saline water.
An aliquot of the liquid is diluted and analysed by electrospray LC/MS/MS.
Evaluation
The concentration of the test and calibration sample are determined by linear regression analysis using a software package such as VG Mass Lynx.

EXAMPLES

All formulations detailed below were coated onto polyurethane foam (EV1700X from Caligen) at a coat weight of 0.8 to 1.6 kg per square meter and cured by exposure to ultraviolet radiation emitted from a medium pressure mercury arc lamp operating at 100 W/cm power for 10 seconds.

Example 1

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add 30 g of glycerol to this and stir for 5 minutes, followed by 40 g of NaAMPS (58%). Stir for another 5 minutes. Add 0.13 g of Solution A and stir the whole formulation for 1 hour before use.

Example 2

Mix 6.0 g of Irgacure 184 with 20 g IRR280 (PEG400 diacrylate) from UCB (Solution A). To 0.07 g of Irgacure 184 add 23.5 g of NNDMA and stir for one hour (keep container covered from light). Add to this 10 g of Mowilith DM137 (50% dispersion of ethylene vinyl acetate copolymer in water from Harco) and stir for 5 minutes. Add 30 g of glycerol to this and stir for 5 minutes, followed by 40 g of NaAMPS (58%). Stir for another 5 minutes. Add 0.13 g of Solution A and stir the whole formulation for 1 hour before use.

Example 3

Mix 6.0 g of Irgacure 184 with 20 g IRR280 (PEG400 diacrylate) from UCB (Solution A). To 0.07 g of Irgacure 184 and 23.5 g of NNDMA and stir for one hour (keep container covered from light). Add to this 10 g of Mowilith DM137 (50% dispersion of ethylene vinyl acetate copolymer in water form Harco) and stir for 5 minutes. Add 30 g of glycerol to this and stir for 5 minutes, followed by 40 g of NaAMPS (58%). Stir for another 5 minutes. Add 0.5 g of Pluronic L64 (poly(ethylene glycol)-block-poly(propylene glycol)-block-poly(ethylene glycol) available from BASF). Add 0.13 g of Solution A and stir the whole formulation for 1 hour before use.

Example 4

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 2 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another five minutes. Add 0.25 g of Pluronic L64 (poly(ethylene glycol)-block-poly(propylene glycol)-block-poly(ethylene glycol) available from BASF). To this add 0.8 g of a 30% aqueous solution of poly(styrene-alt-maleic acid) sodium salt available from Aldrich and stir for 10 minutes. Add 0.13 g of Solution A and stir the whole formulation for 1 hour before use.

Example 5

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.25 g of Pluronic L64 (poly(ethylene glycol)-block-poly(propylene glycol)-block-poly(ethylene glycol) available from BASF). To this add 0.8 g of a 30% aqueous solution of poly(styrene-alt-maleic acid) sodium salt available form Aldrich and stir for 10 minutes. Add 0.13 g of Solution A and stir the whole formulation for 1 hour before use.

Example 6

Mix 6.0 g of Irgacure 184 with 20 g IR280 (PEG400 diacrylate) from UCB (Solution A). To 0.07 g of Irgacure 184 add 23.4 g of NNDMA and stir for one hour (keep container covered from light). Add to this 10 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (58%). Stir for another 5 minutes. Add 0.5 g of Pluronic L64 (poly(ethylene glycol)-block-poly(propylene glycol)-block-poly(ethylene glycol) available from ASF). To this add 0.8 g of a 30% aqueous solution of poly(styrene-alt-maleic acid) sodium salt available from Aldrich and stir for 10 minutes. Add 0.13 g of Solution A and stir the whole formulation for 1 hour before use. Optical phase contrast microscopy showed the resultant gel to have a regularly phase segregated surface (see FIG. 1).

Example 7

Mix 6.0 g of Irgacure 184 with 20 g IRR280 (PEG400 diacrylate) from UCB (Solution A). To 0.07 g of Irgacure 184 add 23.4 g of NNDMA and stir for one hour (keep container covered from light). Add to this 20 g of Mowilith DM137 (50% dispersion of ethylene vinyl acetate copolymer in water from Harco) and stir for 5 minutes. Add 36 g of glycerol to this and stir for 5 minutes, followed by 40.36 g of NaAMPS (50%). Stir for another 5 minutes. Add 0.5 of Pluronic L64 (poly(ethylene glycol)-block-poly(propylene glycol)-block-poly(ethylene glycol) available from BASF). To this add 0.8 g of a 30% aqueous solution of poly(styrene-alt-maleic acid) sodium salt available from Aldrich and stir for 10 minutes. Add 0.13 g of Solution A and stir the whole formulation for 1 our before use.

Example 8

To parts glycerol, were added 40.4 parts of a 58% solution of the sodium salt of 2-acrylamido-2-methylpropane sulphonic acid (NaAMPS) (LZ2405A) together with 0.5 parts Pluronic LF64 (BASF), and the solution stirred to ensure uniform mixing. To the solution was added 0.13 parts of solution containing 20 parts of polyethylene glycol diacrylate (PEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) had been dissolved. A promised solution of 8 parts butyl acrylate and 15.7 parts N,N-dimethylacrylamide (Kohjin) was added to that reaction mixture and this final solution cured by exposure to UV light as in example 1. Optical phase contrast microscopy showed that resultant gel to have a regularly phase-segregated surface and enhanced adhesion to skin that had previously treated with skin cream (Nivea) (see FIG. 2 below).

Example 9

To 30 parts glycerol, were added 0.5 parts of a 30% aqueous solution of poly(styrene-alt-maleic acid) sodium salt available from Aldrich and 40 parts of a 58% solution of the sodium salt of 2-acrylamido-2methylpropane sulphonic acid (NaAMPS) (LZ2405A) together with 0.5 parts Pluronic P65 (BASF), and the solution stirred to ensure uniform mixing. To the solution was added 0.13 parts of solution containing 20 parts of polyethylene glycol diacrylate (PEG600) (product of UCB Chemicals marketed under the trade name Ebycryl 11) in which 6 parts of 1-hydrocycyclohexal phenyl ketone (product of Ciba and marketed under the trade name designation of Irgacure 184) had been dissolved. A premixed solution of 6 parts ethoxyethyl acrylate and 18 parts N,N-dimethylacrylamide (Kohjin) was added so that reaction mixture and this final solution cured by exposure to UV light as in example 5. Optical microscopy showed the resultant gel to have a regularly phase-segregated surface (see FIG. 7 and the associated discussion below).

Results

| Example | Subject 1 Dry ($P_{DI}$) | Subject 1 Greasy ($P_{GI}$) | | Subject 2 Dry ($P_{DI}$) | Subject 2 Greasy ($P_{GI}$) | |
|---|---|---|---|---|---|---|
| | | 1 min | 10 min | | 1 min | 10 min |
| 1 | 1.75 | 0.13 | — | 1.57 | 0.19 | — |
| 2 | 2.96 | 0.16 | — | 3.18 | 0.44 | — |
| 3 | 2.81 | 0.52 | 0.33 | 2.46 | 0.67 | 0.61 |
| 4 | 0.81 | 0.15 | 0.26 | 0.96 | 0.29 | 0.47 |
| 5 | 1.2 | 0.52 | 0.69 | 2.2 | 0.83 | 0.88 |
| 6 | 1.6 | 0.45 | 0.6 | 2.2 | 0.64 | 0.56 |
| 7 | 1.2 | 0.49 | 0.62 | 1.6 | 0.74 | 0.88 |

Microscopy

The gels of Examples 6, 8 and 9 were examined using a Leitz Dialux 20 microscope with a "Wild MPS photoautomat" camera attachment. The microscope was equipped with a 12.5× eyepiece. The image can then be magnified by a number of objectives of which the ×4, ×10 (phaco) and ×25 (phaco) were most commonly used. Both phase contrast and brightfield illumination were used.

Staining

The sample of Example 9 was stained prior to microscopy. A saturated solution of Bromopyrogallol Red in methanol was used to differentially stain the hydrophobic areas of the hydrogel surface. The solution is applied to the surface of the sample, which is then rinsed with methanol to remove any excess dye solution and dye solid. The criteria used in dye selection are outlined below.

The choice of a dye to differentially stain the more hydrophobic and more hydrophilic regions of these gels is influenced by many factors, this may be illustrated by a comparison of Bromopyrogallol Red and fluorescein sodium which are taken up or retained to different extents in different polymer types. The two major factors are charge and hydrophobicity. Bromopyrogallol Red is dominated by acidic —$SO_3H$ and —COOH groups and fluorescein sodium by a slightly acidic —COOH group. More basic regions of the polymer have most affinity for the acidic dye and the acidic regions least affinity for the acidic dye. It can also be observed that a higher water content material allows more rapid uptake of a dye. In conventional hydrogels this is influenced by the fact that higher water content materials will often contain the slightly basic N-vinyl pyrrolidone or N,N-dimethylacrylamide groups which attracts dyes containing acidic groups, e.g. —$SO_3H$ and COOH.

As well as acidity and basicity of the dyes and the polymers, the partition coefficients of the dyes also have a marked effect on the retention of the dyes within the materials. This property is conventionally and commonly characterised by measuring the partition coefficient of the dye between octanol and water ($K_{OW}$). Bromopyrogallol Red has a log $K_{OW}$ of −0.49 and fluorescein sodium has a log $K_{OW}$ of −0.98. Both of the dyes are able to partition between the aqueous and non-aqueous components of the polymers used.

However, Bromopyrogallol Red is more likely to favour the more hydrophobic than the more hydrophilic aqueous phase, in comparison to fluorescein sodium which would prefer the aqueous environment. This preference is illustrated by the fact that conventional N-vinyl pyrrolidone or N,N-dimethylacrylamide based hydrogels tend to retain approximately 30% of the Brompyrogallol Red dye within the polymeric network.

The more intense colour of Brompyrogallol Red coupled with its greater affinity for hydrophobic domains and its solubility in methanol make it much more suited than sodium fluorescein for indicating by differential staining the presence of hydrophobic and hydrophilic regions in the surface of polymer gels.

The invention claimed is:

1. An anti-snoring device (10) comprising:
a flexible sheet of material, wherein said sheet further comprises a central mouth portion (16), a peripheral portion (18), a wearer facing side (12), and an ambient facing side (14), the peripheral portion being defined by two opposing longitudinal edges joining ends of two opposing lateral edges, the central mouth portion being intermediate two opposing lengths of the sheet defined by the two opposing longitudinal edges and intermediate the two opposing lateral edges; and
adhesive coated areas (20), wherein said adhesive coated areas (20) have a total surface area of less than 50% of the total area of said wearer facing side (12),
wherein at least a portion of said mouth portion (16) is adhesive free;
wherein said peripheral portion (18) is provided with a discontinuous application of adhesive on said wearer facing side (12),
wherein said mouth portion is sufficiently rigid to keep a user's mouth closed, during sleep, after application of the anti-snoring device to the wearer's face,
wherein said adhesive free portion of said mouth portion (16) has an area of at least 10% of the total surface area of said wearer facing side (12),
a width of sheet, measured in the longitudinal direction, is in the range of 5 cm to 12 cm,
the lateral edges are smooth lateral edges, and
said adhesive is applied at least on an area of said peripheral portion corresponding to the user's perioral area above the superior lip and on an area of said peripheral portion corresponding to the user's perioral area below the inferior lip.

2. The anti-snoring device (10) of claim 1, wherein said sheet comprises a breathable material, and the peripheral portion is further defined by an oval having two parallel edges joining ends of two opposing smoothly arcuate lateral edges.

3. The anti-snoring device (10) of claim 1, wherein said sheet of material comprises a non-woven material.

4. The anti-snoring device (10) of claim 1, wherein said peripheral portion (18) comprises said adhesive coated areas (20) and adhesive free areas (22), the adhesive coated areas being fabric areas provided with the adhesive and the adhesive free areas being fabric areas free of the adhesive and located longitudinally intermediate the fabric areas provided with the adhesive.

5. The anti-snoring device (10) of claim 1, wherein said adhesive on said wearer facing side (12) is provided as parallel adhesive strips.

6. The anti-snoring device (10) of claim 5, wherein said adhesive strips are horizontally oriented.

7. The anti-snoring device (10) of claim 1, wherein said adhesive has a dry peel strength ($P_{DI}$) and a greasy peel strength ($P_{GI}$) and the ratio of $P_{DI}$ to $P_{GI}$ is from 1:1 to 1.0:0.2.

8. An anti-snoring device (10) of claim 1, wherein said adhesive is placed to permit applying the flexible sheet to a user's mouth area, adhesively attached to the user's perioral area;
wherein said adhesive has dry peel strength ($P_{DI}$) and a greasy peel strength ($P_{GI}$); and,
wherein the ratio of $P_{DI}$ to $P_{GI}$ is from 1:1 to 1.0:0.2,
said adhesive able to adhere to the user's mouth area, after plural reapplications to the user's mouth area, sufficiently to keep the user's mouth closed, during sleep, after further reapplication of the antisnoring device to the wearer's face.

9. The antisnoring device (10) of claim 8, wherein the ratio of said dry peel strength ($P_{DI}$) to said greasy peel strength ($P_{GI}$) is from 1:1 to 1.0:0.3.

10. The anti-snoring device (10) of claim 8, wherein said dry peel strength ($P_{DI}$) ranges from 0.1 N/cm to 5.0 N/cm.

11. The anti-snoring device (10) of claim 10, wherein said greasy peel strength ($P_{GI}$) ranges from 0.1 N/cm to 5.0 N/cm.

12. The anti-snoring device (10) of claim 8, wherein said adhesive is provided as a layer having a thickness, C, measured in millimeters (mm),
wherein said adhesive has a viscous modulus at a temperature of 25° C. (77° F.), $G''_{25}$ (100 rad/sec); and,
wherein said viscous modulus $G''_{25}$ (100 rad/sec) and said thickness, C, of said adhesive satisfy the equation:

$$G''_{25} \text{ (100 rad/sec)} \leq [(7.00+C) \times 3000] \text{ Pa}.$$

13. The anti-snoring device (10) of claim 12, wherein said viscous modulus $G''_{25}$ (100 rad/sec) and said thickness C satisfy the following equation:

$$G''_{25} \text{ (100 rad/sec)} \leq [(5.50+C) \times 1700] \text{ Pa}.$$

14. The anti-snoring device (10) of claim 12,
wherein said adhesive has an elastic modulus at a temperature of 37° C. (100° F.), $G'_{37}$ (1 rad/sec), and a viscous modulus at a temperature of 37° C. (100° F.), $G''_{37}$ (1 rad/sec),
wherein said $G'_{37}$ (1 rad/sec) ranges from 500 Pa to 20000 Pa;
wherein said $G''_{37}$ (1 rad/sec) ranges from 100 Pa to 15000 Pa; and,
wherein the ratio of $G'_{37}$ (1 rad/sec)/$G''_{37}$ (1 rad/sec) ranges from 1 to 30.

15. The anti-snoring device (10) of claim 8,
wherein said adhesive is a substantially water insoluble pressure sensitive adhesive comprising a polymer which forms a 3-dimensional matrix; and,
wherein said adhesive comprises less than 10% by weight of said adhesive of hydrocolloid particles.

16. The anti-snoring device (10) of claim 15, wherein said adhesive further comprises:
a polymer selected from the group consisting of polyacrylics, sulphonated polymers, polyvinyl alcohols, polyvinyl pyrrolidines, polyethylene oxide, and mixtures thereof; and,
a plasticizer selected from the group consisting of polyhydric alcohols, polyethylene glycols, sorbitol, water, and mixtures thereof.

* * * * *